United States Patent [19]

Stack et al.

[11] Patent Number: 5,044,113

[45] Date of Patent: Sep. 3, 1991

[54] MULTI-EDGED RODENT BAIT

[75] Inventors: Malcolm G. Stack, Madison, Wis.; L. Dawn Brown, Richmond, Va.

[73] Assignee: Bell Laboratories, Inc., Madison, Wis.

[21] Appl. No.: 456,101

[22] Filed: Dec. 20, 1989

[51] Int. Cl.$^5$ .............................................. A01M 25/00
[52] U.S. Cl. ........................................... 43/131; 426/1
[58] Field of Search ..................... 43/131; 426/1, 623; 424/410

[56] References Cited

U.S. PATENT DOCUMENTS

| | | | |
|---|---|---|---|
| 944,419 | 12/1909 | Ellis | 424/410 |
| 962,886 | 6/1910 | Bolduan et al. | 424/410 |
| 1,112,755 | 10/1914 | Bergstrom | 43/131 |
| 1,220,593 | 3/1917 | Berg | 424/410 |
| 3,223,231 | 12/1965 | Connolly | 206/568 |
| 3,767,785 | 7/1969 | Bordenca | 43/131 |
| 3,816,610 | 6/1974 | Lusby | 424/419 |
| 3,906,656 | 9/1975 | Burke et al. | 43/131 |
| 4,208,829 | 6/1980 | Manning | 43/131 |
| 4,211,028 | 7/1980 | Roberling | 43/131 |
| 4,581,378 | 4/1986 | Lazar | 424/410 |
| 4,663,882 | 5/1987 | Koljonen | 424/410 |
| 4,793,093 | 12/1988 | Gentile | 606/1 |

FOREIGN PATENT DOCUMENTS 2032164 11/1970 France ................... 43/131

OTHER PUBLICATIONS

Maki Rodenticide Advertisement, *Pest Control*, Aug. 17, 1989, at 17.

*Primary Examiner*—Richard K. Seidel
*Assistant Examiner*—Rex E. Pelto
*Attorney, Agent, or Firm*—Lathrop & Clark

[57] ABSTRACT

A multi-edged rodent bait unit is disclosed having a quantity of rodent meal and rodenticide formed into an extended article having planar front and rear faces. The article has a substantially constant cross section along its length and has four sides perpendicular to the front and rear faces. At least one side has portions defining a V-shaped groove. The walls of the groove meet the faces of the side at angle of less than 150 degrees to form linear edges which are easily gnawed by a rodent. A preferred form of the bait unit has a single groove on each side of the bait unit. A second preferred form has two grooves on each side, and a third preferred form has alternating grooves and ribs. The bait unit of this invention is formed by mixing a rodenticide with rotent meal at room temperature and adding liquid paraffin at approximately 145 degrees Fahrenheit to the mixture and blending the paraffin into the mixture to form a homogeneous mass. The mass is then extruded through a die at high pressures wherein the die has portions to form V-shaped grooves in the sides of the extruded mass. The extruded mass is then cut to desired lengths. The bait unit according to this invention has an increased number of gnawing edges for a rodent to feed upon and is advantageously able to withstand weathering.

10 Claims, 1 Drawing Sheet

MULTI-EDGED RODENT BAIT

FIELD OF THE INVENTION

This invention relates generally to poisoned baits for rodents and in particular to formed multi-faced bait units.

BACKGROUND OF THE INVENTION

Rats, mice, and other rodents are undesirable in human habitations, work places, and agricultural areas. Rodents are commonly exterminated by placing bait units consisting of food impregnated with a rodenticide in areas frequented by rodents. If the rodents can be made to consume the rodent food or bait, they will take the rodenticide as well and will die shortly thereafter.

To be effective, the bait units must be attractive and palatable to the rodents. Rodent bait has been formed in the shape of seeds, as in U.S. Pat. No. 944,419; in the shape of tablets or cylindrical cakes as in U.S. Pat. No. 962,886; and in the form of chunks or crumbs as in U.S. Pat. No. 3,223,231. Bait in very small units has the advantageous property that it fits easily into a rodent's mouth, facilitating rodent consumption of the bait. However, bait in a powdered form or in very small chunks has the drawback that it tends to flow when placed, or be easily dislodged from the baited area. Small bait crumbs can be blown away by winds, can easily be brushed aside or trampled by the rodents, or can be washed away by rain or run-off.

Bait of a small particle size is also more difficult to apply, requiring the user to measure and dispense the bait or place it in a bait container. For these reasons, larger chunks or cubes of bait are often employed. These larger chunks have the advantages of ease of placement and measurement as well as being more stable in their positioning. However, a bait cube on the order of one inch on a side is very large with respect to the mouth of a rodent. As a result, rodents find it difficult to consume the bait, resulting in unused bait or in rodents consuming less than a fatal quantity of rodenticide.

It is also desirable to have a bait unit which can withstand rain, snow, and humidity without rapidly becoming rancid, and hence unpalatable to the rodent. Baits containing high fractions of paraffin show increased weather-resistance, but suffer a commensurate loss in palatability.

What is needed is a rodent bait which is large enough to be conveniently handled and placed, yet which remains palatable and accessible to a rodent. A bait which retains its palatability despite exposure to varying weather conditions is also desirable.

SUMMARY OF THE INVENTION

The rodent bait unit of this invention has a quantity of rodent food and rodenticide extruded into an extended article having a substantially constant cross section along the length of the article. The article has three or more sides and front and rear faces which are preferably perpendicular to the sides. At least one side has portions defining at least one V-shaped groove with inclined walls meeting the side at an inclined angle of not more than approximately 150 degrees. Edges easily gnawed by a rodent are formed where the groove meets the side. A preferred embodiment of the invention has four sides, with one groove on each of at least three sides.

The bait unit of this invention is produced by the method having the steps of first mixing a rodenticide with rodent meal at room temperature, adding liquid paraffin at approximately 145 degrees Fahrenheit to the rodenticide-meal mixture and blending the resultant mixture into a homogeneous mass, then extruding the mass through a die having portions to form V-shaped grooves in the mass at high pressures and cutting off the extruded mass to desired lengths.

It is an object of the present invention to provide a rodent bait unit which is weather-resistant and palatable to rodents.

It is a further object of the present invention to provide a rodent bait unit which is easily gnawed by a rodent.

It is yet another object of the present invention to provide a rodent bait unit having a shape which facilitates consumption by rodents and which may be produced by an extrusion process.

Further objects, features, and advantages of the invention will be apparent from the accompanying detailed description taken in conjunction with the accompanying drawings.

DESCRIPTION OF THE PREFERRED EMBODIMENTS

Figure 1:
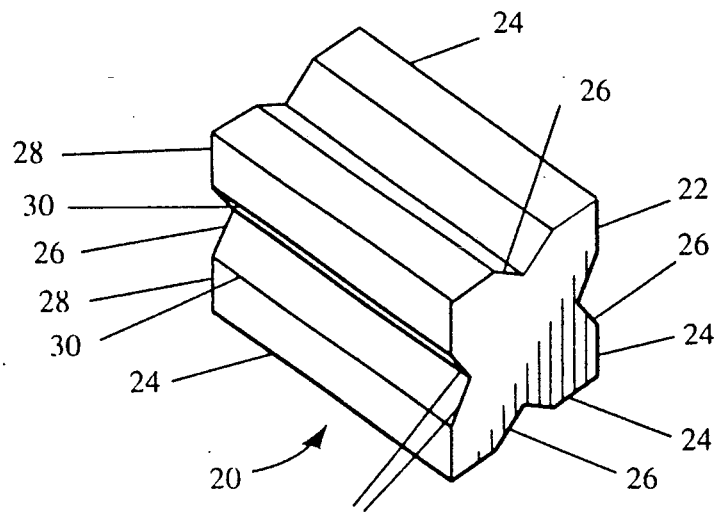
FIG. 1 is an isometric view of a preferred embodiment of the rodent bait unit of this invention.
Figure 2:
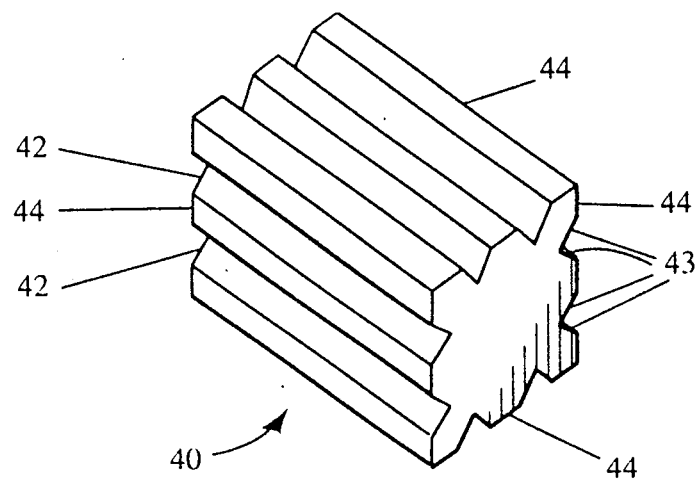
FIG. 2 is an isometric view of a second embodiment of the rodent bait unit of this invention.
Figure 3:
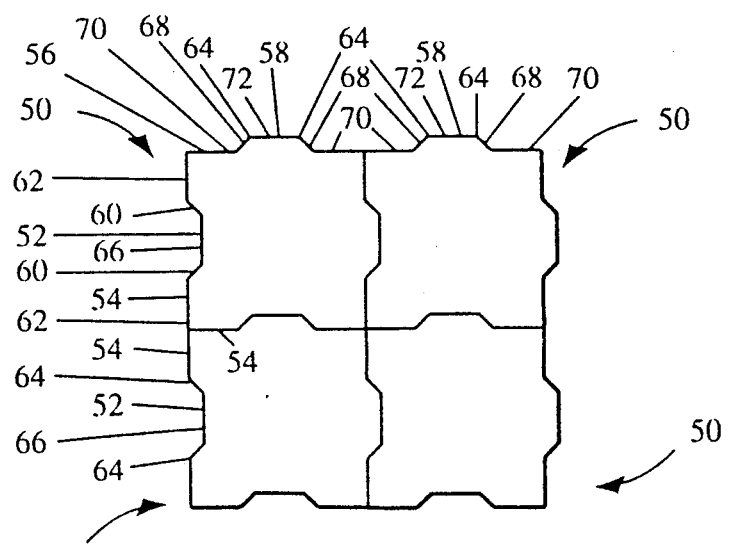
FIG. 3 is a front elevational view of four stacked units of a third embodiment of the rodent bait unit of this invention.

Referring more particularly to FIGS. 1-3 wherein like numbers refer to similar parts, a preferred rodent bait unit 20 is shown in FIG. 1. The bait unit 20 is formed of a quantity of rat meal and rodenticide more fully described below which has been formed into an extended article with three or more and preferably four sides 24. Each side of the bait unit 20 has portions defining a longitudinally extending groove 26. The groove 26 is V-shaped with inclined walls 27 and is preferably centered between the top and bottom of the side 24. The walls 27 of the groove 26 meet the two faces 28 of each side 24 at an angle of approximately 150 degrees. Due to the grooves 26 in the four sides 24 the preferred bait unit has a cross-sectional shape roughly in the form of an "X."

Each bait unit side 24 will typically have a height of about 1 inch, and will be cut to a length of about 2 inches. The bait unit 20 preferably has a planar front face 22 and a planar rear face (not shown), which faces may conveniently extend perpendicularly to the sides 24 to facilitate cutting.

Observations of rodent feeding patterns have shown that rodents will preferentially gnaw at the edges of an object before attempting to eat matter from the planar face of an object. Edges formed by planar surfaces intersecting at an included angle of about 150° or less may be defined as "gnaw edges". Gnaw edges permit rodents to engage the planar surfaces with their teeth on opposite sides of the gnaw edges in opposed fashion to facilitate gnawing of the bait. A simple cube of bait has 12 gnaw edges, one at each intersection of faces of the cube. However, only eight of the gnaw edges of a cube are accessible to a rodent when the cube is placed on a supporting surface, such as the floor of a bait station. The bait unit 20 of this invention increases the acceptability of the bait to the rodent by providing significantly increased lengths of gnaw edges 30. Each groove 26 adds six gnaw edges 30 to the bait unit 20—a gnaw edge where each face 28 of the side 24 meets the groove 26, two additional gnaw edges where the groove meets the front face 22, and two more gnaw edges where the groove 26 meets the rear face. A bait unit 20 having four grooved sides 24 will have a total of 32 gnaw edges 30 at which a rodent may begin to eat the bait, 26 of which are fully accessible to a rodent when the bait unit 20 is placed on a supporting surface. The groove 26 on the side 24 which rests on a supporting surface is not accessible to a rodent, and accordingly, the groove 26 may be eliminated on the side 24 of the bait unit 20. The side 24 without a groove 26 will then be the bottom side of the bait unit 20 to be placed on the supporting surface. It is not uncommon for a bait unit 20 to be tipped or rotated 90 degrees by the action of rodent feeding. In such a case, if all four sides 24 of the bait unit 20 have a groove 26, the bottom gnaw edges would then be presented to the rodent.

In order for a bait unit to be acceptable to a rodent, it must contain food ingredients which are palatable to the rodent. Well-known rodent feeds include cereal products, wheat flour, whole seeds, vegetable oils, and flavor enhancers. Preservatives and artificial coloring are added to the bait to preserve the freshness and make the bait more attractive to the rodent. None of these ingredients are harmful to the rodents. These nonharmful ingredients are commonly termed "inert ingredients" of a bait, and normally make up more than 98 percent of the bait unit. It is necessary to add only a small fraction of an "active ingredient" rodenticide to the bait unit to effectively poison the rodents. Typically, this active ingredient may be an anticoagulant such as diphacinone or bromadiolone or any other acute or chronic rodenticide.

To form the bait unit 20 the food ingredients are mixed at room temperature with the active ingredient, the preservatives and the artificial colorings. Paraffin amounting to 20 to 40 percent of the combined weight of the ingredients is heated to above its melting point and added to the mixture. Paraffin is acceptable to rodents and aids in the cohesion of the ingredients in the bait unit. The liquid paraffin and the other ingredients are blended into a homogeneous mixure which is at a temperature of about 100 degrees Fahrenheit. This homogeneous mass is then metered through a forming extruder at high pressures to produce the shaped bait unit. The extruding die has the same profile as the desired final bait unit. Lengths of extruded bait may be cut off to form appropriately-sized bait units. The units are then allowed to set up to attain their final firmness.

The extruded bait units 20 have tightly packed sides with grooves that will not crumble easily. This tight packing ensures that the gnaw edges will remain prominent until fully consumed by the rodent.

The bait units formed by this process are able to withstand exposure to moisture and the elements for an extended period of time before the bait becomes rancid and unacceptable to the rodent.

A second preferred embodiment of the multi-edged rodent bait of this invention is shown in FIG. 2. The bait unit 40 is formed in the same manner as the bait unit 20, but is extruded with two grooves 42 on each side 44. These V-shaped grooves 42 preferably obtain a depth of ⅛ of an inch and have groove sides 43. By providing eight grooves on the bait unit 40, a total of 60 gnaw edges are provided for rodent feeding. It should be noted with respect to both bait units 20 and 40 that the gnaw edges formed at the intersections of the groove 26 and the front and rear faces do not constitute total additions to the length of gnawing edges 30 on the bait which, because portions of the gnawing edges formed between the sides and end faces of the bait unit are omitted by the grooves 26. However, the gnaw edges at the ends of each groove 26 together are of greater length than the omitted gnaw edge portions, and represent a significant addition to the length of the gnaw edges on the bait unit 20.

A third embodiment of the multi-edged rodent bait of this invention is shown in FIG. 3. The bait units 50 each have two adjacent sides 54 with longitudinal grooves 52, and two adjacent sides 56 which have longitudinal ribs 58. The grooves 52 have side walls 60 which form an included angle of approximately 135° with the faces 62 of each side 54 to form gnaw edges 64. The grooves 64 are preferably about ⅛ inch deep, and have a flat floor 66 having a width of approximately ¼ inch. The ribs 58 have side walls 68 which extend outwardly from the faces 70 of sides 56 at an angle of approximately 45°, and flat tops 72 which form an included angle of approximately 135° with each of the rib side walls 68 to form additional gnaw edges 64. As further shown in FIG. 3, the ribs 58 are the same cross-sectional shape as the grooves so that the bait units 50 may be stacked for storage or transport rib to groove in dense, nested manner with no wasted air space except at the edges of the stack. The bait units 50 illustrate that the increased elongate gnaw edges may be provided by ribs as well as grooves on a planar surface.

Alternate forms of the bait unit having varying numbers of grooves on each side or having certain sides grooveless are also possible.

EXAMPLES

The acceptability to rodents and the effectiveness of a bait unit of this invention was tested in the following two experiments. In both experiments the bait unit had three grooves—one on each exposed side of the extruded bait unit. The bait units used weighed approximately 1 ounce and were 15/16 inches on a side and 1 and ¾ inches long. The V-shaped grooves were ⅛ of an inch deep.

In the first experiment, the results of which are shown in Table 1, ten Wistar rats were individually caged and provided water as needed. Rats were able to choose between an EPA challange diet and the bait unit which contained Bromadiolone as the active ingredient. After the first day the rats preferred the poisoned bait unit resulting in fatalities of all the rodents in 13 days.

TABLE 1

| Test Days | % Test Diet | Test Diet (g) | Control Diet (g) | Total Diet (g) | % Mortality |
| --- | --- | --- | --- | --- | --- |
| 1 | 43.8 | 108.4 | 139.2 | 247.6 | |
| 2 | 61.0 | 123.2 | 78.8 | 202.0 | |
| 3 | 73.7 | 125.5 | 44.8 | 170.3 | 20 |
| 4 | 75.3 | 72.5 | 23.8 | 96.3 | 10 |
| 5 | 65.6 | 13.9 | 7.3 | 21.2 | 10 |
| 6 | 85.9 | 5.5 | 0.9 | 6.4 | 30 |
| 7 | 100 | 1.4 | 0 | 1.4 | 20 |
| 8 | 100 | 1.9 | 0 | 1.9 | |
| 9 | 87.0 | 2 | 0.3 | 2.3 | |
| 10 | 81.4 | 3.5 | 0.8 | 4.3 | |
| 11 | 85.1 | 6.3 | 1.1 | 7.4 | |

TABLE 1-continued

| Test Days | % Test Diet | Test Diet (g) | Control Diet (g) | Total Diet (g) | % Mortality |
| --- | --- | --- | --- | --- | --- |
| 12 | 67.0 | 7.7 | 3.8 | 11.5 | |
| 13 | | 0 | 0 | 0 | 10 |
| Total Mortality (%) | | | | | 100 |
| Total Consumed (g) | | 471.8 | 300.8 | 772.6 | |
| Amounts Consumed (% of total) | | 61.1 | 38.9 | 100.0 | 100 |

In the second test, the results of which are shown in Table 2, ten Swiss Webster mice were group caged and presented with a choice of an EPA challenge diet or the bait unit as described above with Diphacinone as the active ingredient. From the first day the mice preferred the poisoned bait unit resulting in 100 percent fatalities in 11 days.

TABLE 2

| Test Days | % Test Diet | Test Diet (g) | Control Diet (g) | Total Diet (g) | % Mortality |
| --- | --- | --- | --- | --- | --- |
| 1 | 51.6 | 33.5 | 31.4 | 64.9 | |
| 2 | 71.5 | 37.2 | 14.8 | 52 | |
| 3 | 51.0 | 13.4 | 12.9 | 26.3 | |
| 4 | 69.1 | 3.8 | 1.7 | 5.5 | 20 |
| 5 | 56.6 | 1.3 | 1 | 2.3 | 30 |
| 6 | | 0 | 0 | 0 | 20 |
| 7 | 100 | 0.2 | 0 | 0.2 | |
| 8 | 78.8 | 2.6 | 0.7 | 3.3 | |
| 9 | | 0 | 0.6 | 0.6 | 10 |
| 10 | | 0 | 0 | 0 | 10 |
| 11 | | 0 | 0 | 0 | 10 |
| Total Mortality (%) | | | | | 100 |
| Total Consumed (g) | | 92 | 63.1 | 155.1 | |
| Amounts Consumed (% of total) | | 59 | 40 | 100 | |

It is understood that the present invention is not limited to the particular embodiments disclosed and illustrated herein, but embraces all such modified forms thereof as come within the scope of the following claims.

I claim:

1. A rodent bait unit, comprising:
   (a) an extruded quantity of rodent meal and rodenticide formed into an extended article having at least three planar sides and a substantially constant cross-section along the length of the unit, wherein at least two sides have portions therein defining at least one V-shaped groove in each side with two inclined planar walls, and each side with a groove has planar faces which each intersect an inclined planar wall of a V-shaped groove at an included angle of not more than approximately 150 degrees, wherein the intersections of the planar faces and the inclined planar walls form gnaw edges which permit rodents to engage the intersecting planar faces and walls with their teeth in opposed fashion to facilitate gnawing of the bait unit, and wherein the bait unit has a front face and a rear face and the planar faces of the sides intersect the front and rear faces to form gnaw edges and the inclined planar walls of the grooves intersect the front and rear faces to form increased gnaw edges.

2. The rodent bait unit of claim 1 further comprising a V-shaped groove on each side.

3. The rodent bait unit of claim 1 wherein the rodent meal is composed of a mixture of cereal products, flour, whole seeds, vegetable oils, preservatives, flavor enhancers, artificial color and paraffin, and the rodenticide is an anti-coagulant.

4. The rodent bait unit of claim 1 wherein each groove has a depth of at least ⅛ of an inch.

5. The rodent bait unit of claim 1 wherein the front and rear faces extend perpendicularly to the sides.

6. The rodent bait unit of claim 1 having four sides.

7. A method of producing a rodent bait unit, comprising the steps of:
   (a) mixing a rodenticide with rodent meal at room temperature;
   (b) adding liquid paraffin to the rodenticide-meal mixture and blending into a homogeneous mass;
   (c) extruding the mass through a die at high pressures, wherein the die has portions which form an extended bait unit having at least three planar sides and a substantially constant cross-section along the length of the unit, at least two formed sides having indented V-shaped grooves with two inclined planar walls, wherein each side with a groove is extruded to have planar faces which intersect the inclined planar walls of the V-shaped grooves at an included angle of not more than approximately 150°, wherein the intersections of the planar faces and the inclined planar walls form gnaw edges which permit rodents to engage the intersecting planar faces and walls with their teeth in opposed fashion to facilitate gnawing of the bait unit; and
   (d) cutting off the extruded mass to desired lengths to form bait units having a planar front face and a planar rear face.

8. The process of claim 7 wherein the rodent meal comprises a mixture of cereal products, flour, seeds, vegetable oils, preservatives, and flavor enhancers.

9. The process of claim 7 wherein the step of adding paraffin to the mixture comprises adding paraffin to achieve 20 to 40 percent by weight of the mixture.

10. A rodent bait unit comprising:
   (a) a quantity of tightly packed rodent meal, rodenticide and parafin formed into an extended article of substantially constant cross section along the length of the unit, and having four sides; and
   (b) wherein each side has portions therein defining at least two V-shaped grooves each of which has two inclined planar walls, and each side has a plurality of planar faces which each intersect at least one inclined planar wall of a V-shaped groove at an included angle of not more than 150°, wherein the intersections of the planar faces and the inclined planar walls form a plurality of gnaw edges dimensioned to permit rodents to engage the intersecting planar faces and walls with their teeth in opposed fashion to facilitate gnawing of the bait unit, and wherein the bait unit has a front face and a rear face and the planar faces of the sides intersect the front and rear faces to form gnaw edges and the inclined planar walls of the grooves intersect the front and rear faces to form increased gnaw edges.

* * * * *